United States Patent [19]

Hupp

[11] Patent Number: 4,515,965

[45] Date of Patent: May 7, 1985

[54] PROCESS FOR PREPARING MALEIMIDE

[75] Inventor: Stephen S. Hupp, Dublin, Ohio

[73] Assignee: Ashland Oil, Inc., Ashland, Ky.

[21] Appl. No.: 579,063

[22] Filed: Feb. 10, 1984

[51] Int. Cl.³ .................................. C07D 207/448
[52] U.S. Cl. ................................................ 548/548
[58] Field of Search ...................................... 548/548

[56] References Cited

FOREIGN PATENT DOCUMENTS 128371 7/1983 Japan ................................ 548/508
569568 8/1977 U.S.S.R. .

Primary Examiner—Glennon H. Hollrah
Assistant Examiner—D. B. Springer
Attorney, Agent, or Firm—John F. Jones

[57] ABSTRACT

A process for the preparation of maleimide by the vapor phase oxydehydrogenation of succinimide over an iron phosphate catalyst which may also contain one or more alkali metal and alkaline earth metal components is described.

7 Claims, No Drawings

PROCESS FOR PREPARING MALEIMIDE

This invention relates to a method for the preparation of maleimide and more particularly pertains to the oxidative dehydrogenation of succinimide in the vapor phase over a specified heterogeneous catalyst to form maleimide in good yields.

Maleimide, also known as maleic acid imide, is a well-known material which has been used as a monomer in the manufacture of homopolymers and copolymers and also as a fungicide and bactericide. Because of the lack of prior methods for the production of maleimide in good yields and resultant high cost, it is believed that this material has not been utilized as fully as it might have been in the past.

Heretofore, maleimide has been prepared by the ammonolysis of maleic anhydride followed by dehydration over dehydration catalysts as in British Pat. No. 1,123,515. Maleimide has also been prepared by the ammoxidation of butadiene as disclosed in Japanese Patent No. 42-269.3 (1967), and by the oxidative dehydrogenation of succinimide over a vanadium oxide or vanadium oxide-titanium dioxide catalyst as in USSR inventor's certificate No. 569,568

I have discovered that maleimide can be prepared in good yields by the oxidative dehydrogenation of succinimide (succinic acid imide) in the presence of air and water and in the presence of a heterogeneous catalyst having the formula Fe $P_x Me_y O_z$ wherein Me is one or more of the elements Li, Na, K, Rb, Cs, Mg, Ca, Sr, and Ba, x is from 0.2–3.0, y is from 0–2 and z is the value corresponding to average valences of the elements in the oxidation states in which they exist in the catalyst, in the temperature range of from 300° to 550° C., and in the pressure range of from 0.1 to 10 atmospheres. Catalysts of this type and methods for their preparation are known to those skilled in the art, for instance, see U.S. Pat. No. 3,948,959.

In my process, the succinimide:Air:water molar ratios can vary from 1:0.1:1 to 1:5:50, respectively.

The heterogeneous catalysts of my process can be more specifically described as iron phosphates which also can contain one or more alkali metal and alkaline earth metal components. The catalysts useful in my invention are preferably calcined at a temperature in the range of from 300° to 600° C. for an hour or more.

The process of this invention is further illustrated in the following representative examples.

EXAMPLE 1

A 10.51 g. quantity of a catalyst having the composition $FeCs_{0.15}P_{1.23}O_x$/3% $SiO_2$ (i.e., 3% by weight of the catalyst was a silica carrier) which had been calcined at 100° C. overnight, 250° C. for 4 hours, 350° C. for 2 hours and then at 500° C. for about 16 hours, and having a mesh size of 12/20 which was also mixed with 23.34 g of 12/20 mesh quartz chips and was placed in a tubular fixed bed catalytic reactor measuring 8" in length with an ID of ⅜". While the reactor temperature was maintained at 450° C. and the pressure was about atmospheric, an aqueous feed containing 100 g. of succinimide per 273 g. of water and 0.1% hydroquinone was fed to the reactor at a rate of 22.9 g./hour with air fed at the rate of 77 cc/min. The effluent from the reactor was collected in two portions. The first for 130 minutes and the second for 113 minutes. The products were washed from the collection flasks with water and combined to give a total of 343.86 g. of dark red-brown aqueous solution. A 172.77 g. portion of this aqueous solution was extracted three times with separate ethyl acetate portions to give a total of 333.80 g. of ethyl acetate solution containing the product maleimide. Analysis of the ethyl acetate solution by G.C. showed that it contained 2.601 wt.% or 8.681 g. of maleimide which represents a 68.8% yield of maleimide from succinimide. The G.C. analysis also showed that the solution contained 0.034 wt.% or 0.113 g. of succinimide indicating a conversion of succinimide of about 99%.

EXAMPLE 2

The procedure of Example 1 was repeated except that the catalyst was $FePO_4$ and the reactor temperature was in the range of 397°–459°. This procedure gave a conversion of succinimide of 99%, a selectivity to maleimide of 56.7% and an overall yield of maleimide of 56.2%.

EXAMPLE 3

The procedure of Example 1 was repeated except that the catalyst was $FeK_{0.23}P_{1.45}O_x$ and the reactor temperature was in the range of 447°–456° C. The reaction produced a conversion of succinimide of 70%, a selectivity to maleimide of 67% and an overall yield of maleimide of 47%.

EXAMPLE 4

The procedure of Example 1 was repeated except that the catalyst was $FeSrP_{1.4}O_x$ and the reactor temperature was in the range of 495°–507° C. The reaction produced a conversion of succinimide of 51%, a selectivity to maleimide of 85% and an overall yield of maleimide of 43%.

I claim:

1. A process for the preparation of maleimide consisting essentially of subjecting a mixture of succinimide, air and water to oxidative dehydrogenation at a temperature in the range of from 300° to 550° C. over a catalyst having the formula $FeP_xMe_yO_z$ wherein Me is one of more of the elements Li, Na, K, Rb, Cs, Mg, Ca, Sr and Ba; x is from 0.2–3.0; y is from 0–2 and z is the value corresponding to average valences of the elements in the oxidation states in which they exist in the catalyst.

2. The process of claim 1 carried out in the pressure range of from 0.1 to 10 atmospheres.

3. The process of claim 2 wherein the mole ratios of succinimide:air:water are in the range of 1:10.1:1 to 1:5:50, respectively.

4. The process of claim 3 wherein the catalyst is $FeCs_{0.15}P_{1.23}O_x$/3%$SiO_2$.

5. The process of claim 3 wherein the catalyst is $FePO_4$.

6. The process of claim 3 wherein the catalyst is $FeK_{0.23}P_{1.45}O_x$.

7. The process of claim 3 wherein the catalyst is $FeSrP_{1.4}O_x$.